United States Patent [19]

Takahashi

[11] 4,195,528
[45] Apr. 1, 1980

[54] FAULT DETECTION DEVICE

[75] Inventor: Yasuhide Takahashi, Amagasaki, Japan

[73] Assignee: Mitsubishi Denki Kabushiki Kaisha, Tokyo, Japan

[21] Appl. No.: 924,829

[22] Filed: Jul. 14, 1978

[30] Foreign Application Priority Data

Jul. 18, 1977 [JP] Japan ............................. 52/86429

[51] Int. Cl.² .......................................... G01H 13/00
[52] U.S. Cl. .................................... 73/579; 73/649; 116/200
[58] Field of Search ............. 73/570, 571, 572, 574, 73/577, 579, 649, 652, 660, DIG. 1; 116/114 R, 114 C, 114 D, 114 AH, 200; 331/156; 340/261

[56] References Cited

U.S. PATENT DOCUMENTS

| 2,932,189 | 4/1960 | Carlin | 73/570 |
| 2,974,521 | 3/1961 | Phelps | 73/652 X |
| 3,698,351 | 10/1972 | Harrah et al. | 116/114 D X |
| 3,705,516 | 12/1972 | Reis | 73/660 X |
| 3,878,858 | 4/1975 | Yamada | 116/114 D X |
| 3,903,733 | 9/1975 | Murayama et al. | 73/574 |
| 3,979,739 | 9/1976 | Birchall | 73/660 X |
| 4,058,134 | 11/1977 | Kamatsu et al. | 116/114 D X |

FOREIGN PATENT DOCUMENTS 767670 2/1957 United Kingdom ................ 340/683

*Primary Examiner*—Donald Watkins
*Attorney, Agent, or Firm*—Wenderoth, Lind & Ponack

[57] ABSTRACT

A U-shaped tuning fork is fixed to a supporting block connected to a body in which a fault is to be detected. A spring loaded rod is movably supported at one end on the supporting block and extends through a spherical wedge sandwiched between two legs of the tuning fork. The tuning fork resonates at a frequency at which the detected body vibrates when a fault occurs in it. This permits the wedge and therefore the rod to move indicating the occurrence of the fault. Simultaneously a microswitch is operated to indicate electrically the existence of the fault.

9 Claims, 2 Drawing Figures

FAULT DETECTION DEVICE

BACKGROUND OF THE INVENTION

This invention relates to a fault detection device for faults occurring in detected bodies such as electrical appliances, vessels, aircraft etc.

In large-scale electrical appliances, transformer substations, various plants, machine tools, vessels, aircraft etc, detecting a fault or faults occurring in the entire equipment or a specified part thereof is very important in view of the standpoint that urgent countermeasures be taken against the fault or faults to prevent the spread thereof and the occurrence of secondary calamities.

Machines and apparatus of the type referred to in many cases generate vibrations during operation but when an abnormality occurs therein, the vibration frequency is generally varied and/or the acceleration due to the vibration becomes very high.

It is an object of the present invention to provide a new and improved fault detection device for immediately detecting a fault in a body by sensing a characteristic change in acceleration due to a vibration resulting from an abnormality occurring in the body which device has a simple construction and yet has a high reliability.

It is another object of the present invention to provide a new and improved fault detection device responsive to a fault but not to any external disturbance and which is extremely stable in operation and does not malfunction.

It is still another object of the present invention to provide an inexpensive fault detection device which eliminates the necessity of employing expensive devices such as a sensor, an amplifier etc utilizing electronics.

SUMMARY OF THE INVENTION

The present invention provides a fault detection device comprising a resonator resonating at a predetermined vibration frequency corresponding to that of the body in which a fault is to be detected, a detection element carried by the resonator and the movement of which is limited, and a resilient member tending to move the detection element in a predetermined direction, the resonator resonating in cooperation with the resilience provided by the resilient member to move the detection element in the predetermined direction thereby to detect a fault occurring in the body.

In a preferred embodiment of the present invention the resonator may includes a pair of spaced opposed holders vibrating by resonating at the predetermined vibration frequency, to increase the space therebetween by means of the vibration and the detection element is sandwiched between the holders.

BRIEF DESCRIPTION OF THE DRAWING

The present invention will become more readily apparent from the following detailed description taken in conjunction with the accompanying drawing in which.

DESCRIPTION OF THE PREFERRED EMBODIMENT

Figure 1:
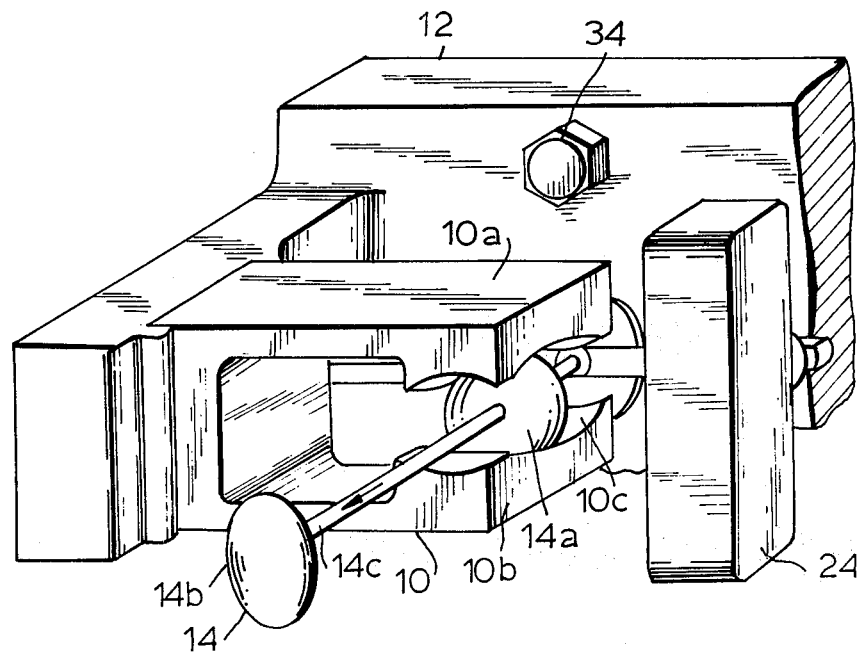
FIG. 1 is a perspective view of one embodiment of the fault detection device according to the present invention.

Referring now to the drawing there is illustrated a fault detection device according to the present invention. The arrangement illustrated comprises a resonator 10 in the form of a U-shaped tuning fork including a pair of spaced opposed legs 10a and 10b, an L-shaped supporting block 12 having the resonator 10 rigidly secured to one leg of the "L" and a detector element generally designated by the reference numeral 14, and carried between the legs 10a and 10b of the tuning fork. The detection element 14 includes a spherical wedge 14a engaging a pair of recesses disposed on the opposed inner surfaces of the free end portions of both legs 10a and 10b, a combined indication and reset button 14b and a connection rod 14c connected to the button 14b and fixed to and extending through the center of the spherical wedge 14a. The leg 10a or 10b called a holder. As best shown in FIG. 2, the connection rod 14c has the other end portion inserted into the other leg of the L-shaped block 12 for a limited longitudinal movement therein and includes a helical spring 16 disposed between the other leg of the block 12 and a spring retainer 18 connected to the rod 14c on that side thereof remote from the button 14b and around the rod 14c. The spring 16 tends to move the resonator 14 in the direction of the arrow shown in FIG. 1.

As shown in FIG. 2, a lever 20 is rotatably secured to a hinge 22 fixed to the one leg of the L-shaped supporting block 12 and engages the detection element 14. The lever 20 interlocks with the detection element 14 so that it is urged toward a microswitch 24 by the retainer 18 receiving the force exerted by the helical spring 16 until it engages an operating button 24a to operate the microswitch 24.

The components as above described are housed in a casing 26 that includes a window 28 facing the button 14b and closed with a foil formed, for example, of aluminum and an open end snugly fitted onto the other leg of the U-shaped supporting block 12 and fixed thereto by a plurality of screws 30, only two of which are illustrated.

Figure 2:
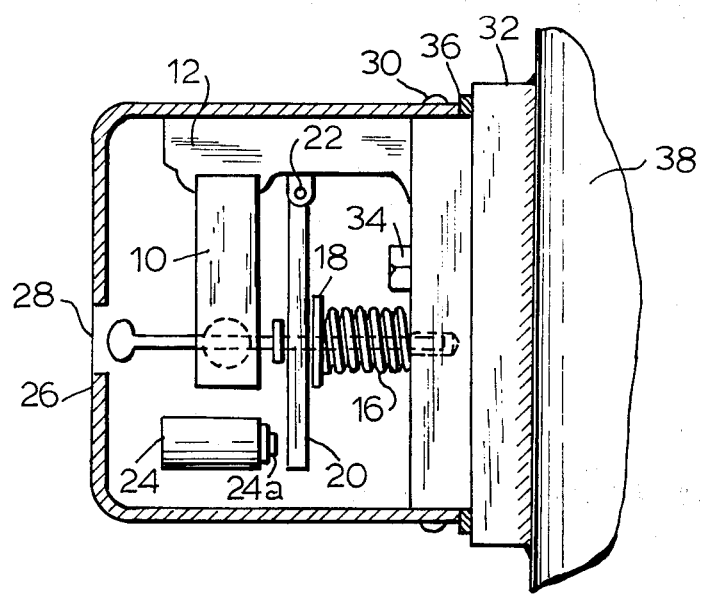
FIG. 2 is a plan view, partly in section of the arrangement shown in FIG. 1 and mounted on a body the vibration of which is to be detected.

Then the arrangement shown in FIG. 1 is mounted on a mounting seat 32 by means of a mounting bolt 34 with a packing 36 interposed between the casing 26 and the seat 32. Then the mounting seat 32 is fixedly secured to a body 38 in which a fault is to be detected. When the arrangement of FIG. 1 is used in the open air, the packing 36 serves to prevent rain and dew from entering the interior of the casing 26.

The arrangement shown in FIG. 2 operates as follows: It is assumed that a fault has occurred in the body 38 causing the latter to vibrate at a predetermined frequency. This vibration is transmitted to the U-shaped tuning fork or resonator 10 through the mounting seat 32 and the block 12. The legs 10a and 10b of the U-shaped tuning fork 10 resonate at that predetermined frequency and the acceleration due to the resonance is at a level far higher than that in the normal operation. Therefore the amplitude of vibration of the tuning fork 10 increases rapidly whereby the spacing between the legs 10a and 10b increases. As a result, a frictional force developed between the spherical wedge 14a and the legs 10a and 10b to hold the wedge 14a between those legs rapidly decreases until the resilience of the helical spring 16 overcomes this decreased frictional force and causes the detection element 14 or the spherical wedge 14a to move in the direction of the arrow shown in FIG. 1. This movement of the detection element 14 causes the combined indication and reset button 14b to break the foil over the window 28 and to protrude externally of the casing 26. Thus the occurrence of the fault has been indicated.

On the other hand, upon movement of the detection element 14 the helical spring 16 also rotates the lever 20 in a clockwise direction as viewed in FIG. 2 until it engages the operating button 24a to operate the microswitch 24. The microswitch 24 produces an ON or an OFF electrical signal serving to drive an alarm or an alarm lamp disposed at a remote position to indicate the occurrence of the fault.

Thereafter the button 14b can be depressed and a new foil placed over the window 28 to be ready for the next succeeding operation.

The present invention has several advantages. For example, the present invention can be made from a small number of structural components which are also inexpensive. Further the present invention can be made to be responsive to both a predetermined frequency of vibration and an acceleration in excess of a certain magnitude and therefore is extremely stable and not subject to malfunction and not responsive to any external disturbance such as an earthquake shock, the striking of the body in which a fault is being detected with a hammer or the like. Further the present device is inexpensive because it does not use a sensor, an amplifier or the like utilizing electronics. In addition, the present device can be used in a stabilized state and a special shielding or protective circuit is not required to be inserted between the present invention and equipment generating external electromagnetic distirbances.

While the present invention has been illustrated and described in conjunction with a single preferred embodiment thereof it is to be understood that numerous changes and modifications may be resorted to without departing from the spirit and scope of the present invention. For example, either the mechanical indicator such as the button 14b or the microswitch with the associated components may be omitted.

What is claimed is:

1. A fault detection device for detecting a fault in a body, said device comprising: a resonator resonating at a predetermined vibration frequency at which the body in which the fault is to be detected vibrates when a fault is present in it, a detection element carried by said resonator and held against movement by said resonator at vibration frequencies other than the resonant frequency of said resonator, and a resilient member engaging said detection element and urging said detection element in a predetermined direction, said resonator freeing said detection element sufficiently when vibrating at the resonant frequency for the resilience of said resilient member to move said detection element in said predetermined direction to thereby indicate the detection of a fault in the body.

2. A fault detection device as claimed in claim 1 wherein said resonator has a pair of spaced opposed holders vibrating resonantly at said predetermined vibration frequency for increasing the space therebetween and said detection element is sandwiched between said holders.

3. A fault detection device as claimed in claim 2 wherein said detection element includes a spherical wedge and said holders have opposed recesses in the opposed faces in which said spherical wedge is held.

4. A fault detection device as claimed in claim 3 in which said resonator is a tuning fork and said holders are the legs thereof.

5. A fault detection device as claimed in claim 1 wherein said detection element includes a first portion held by said resonator, and a second portion integral with said first portion for indicating the movement of said detection element, said second portion being returnable to its original position prior to movement of said detection element indicating detection of a fault against the resilience of said resilient member.

6. A fault detection device as claimed in claim 5 further comprising a casing within which said resonator, said detection element and said resilient member are disposed, said casing having a window therein in a portion thereof opposed to said second portion of said detection element, and a metallic foil closing said window, said second portion of said detection element moving through said window for rupturing said foil when said resonator vibrates at said predetermined frequency.

7. A fault detection device as claimed in claim 1 further comprising a supporting block to which said resonator is fixedly secured, and a lever rotatably mounted on said supporting block and engaged by said detection element for movement in response to movement of said detection element, and a microswitch engaged by said lever when said lever is moved.

8. A fault detection device as claimed in claim 7 wherein said resilient member is a helical spring disposed between said lever and said supporting block.

9. A fault detection device as claimed in claim 1 further comprising a supporting block having said resonator fixed thereto and a casing secured to said supporting block and accommodating said resonator, said detection element and said resilient member therein, a mounting seat on which said supporting block is mounted and for attaching said device to the body, and a water tight packing between said casing and said mounting seat.

* * * * *